US012634577B1

(12) United States Patent
Gupta et al.

(10) Patent No.: US 12,634,577 B1
(45) Date of Patent: May 19, 2026

(54) SYSTEMS AND METHODS FOR AUTOMATED PROFILE IDENTIFICATION

(71) Applicant: Pramana, Inc., Cambridge, MA (US)

(72) Inventors: Raghubansh Bahadur Gupta, Bangalore (IN); Tushar Singh, Bangalore (IN); Rohan Prateek, Uttar Pradesh (IN); Venkata Veera Lokesh Kumar Puvvada, Guntur (IN); Sai Pranav Varada Raghunath, Andhra Pradesh (IN); Prasanth Perugupalli, Cary, NC (US)

(73) Assignee: Pramana, Inc., Cambridge, MA (US)

( * ) Notice: Subject to any disclaimer, the term of this patent is extended or adjusted under 35 U.S.C. 154(b) by 0 days.

(21) Appl. No.: 19/176,697

(22) Filed: Apr. 11, 2025

(51) Int. Cl.
| | |
|---|---|
| *H04N 23/60* | (2023.01) |
| *G06V 10/82* | (2022.01) |
| *G06V 20/62* | (2022.01) |
| *G06V 20/69* | (2022.01) |
| *G06V 30/10* | (2022.01) |
| *G16H 10/40* | (2018.01) |
| *G16H 40/40* | (2018.01) |
| *H04N 23/667* | (2023.01) |

(52) U.S. Cl.
CPC ............. *H04N 23/64* (2023.01); *G06V 10/82* (2022.01); *G06V 20/62* (2022.01); *G06V 20/698* (2022.01); *G06V 30/10* (2022.01); *G16H 10/40* (2018.01); *G16H 40/40* (2018.01); *H04N 23/667* (2023.01)

(58) Field of Classification Search
CPC ...... H04N 23/64; H04N 23/667; G16H 10/40; G16H 40/40; G06V 30/10; G06V 20/62; G06V 20/698; G06V 10/82
See application file for complete search history.

(56) References Cited

U.S. PATENT DOCUMENTS

| | | | |
|---|---|---|---|
| 6,215,892 B1 * | 4/2001 | Douglass | G02B 21/367 |
| | | | 382/128 |
| 10,762,630 B2 | 9/2020 | Yaqub et al. | |
| 11,978,185 B1 | 5/2024 | Perugupalli et al. | |
| 11,983,874 B1 | 5/2024 | Dodle et al. | |
| 11,997,240 B1 | 5/2024 | Perugupalli et al. | |
| 12,281,357 B1 * | 4/2025 | Tentori | C12Q 1/6876 |
| 2007/0031056 A1 | 2/2007 | Perz | |

(Continued)

FOREIGN PATENT DOCUMENTS

| | | |
|---|---|---|
| CN | 112464802 A | 3/2021 |
| WO | 2021189771 A1 | 9/2021 |

*Primary Examiner* — Peet Dhillon
(74) *Attorney, Agent, or Firm* — CALDWELL LLC

(57) ABSTRACT
A system including at least an imaging device and a computing device configured to control the at least an imaging device while pre-scanning the target, receive, from the at least an imaging device, the pre-scan imaging data, detect a position of the fiducial marker within the pre-scan imaging data, input the pre-scan imaging data into a feature-learning neural network, output at least an image feature from the feature-learning neural network as a function of the pre-scan imaging data, wherein the at least a feature represents at least a specimen type, selecting a target profile as a function of the specimen type and the fiducial marker, wherein the target profile includes one or more imaging parameters and adjust, using the target profile, one or more imaging device parameters as a function of the one or more imaging parameters.

18 Claims, 7 Drawing Sheets

(56) References Cited

U.S. PATENT DOCUMENTS

| 2007/0054350 A1* | 3/2007 | Walker | G06V 20/69 |
| | | | 382/128 |
| 2007/0139638 A1* | 6/2007 | Wolpert | G06V 10/141 |
| | | | 356/39 |
| 2011/0249910 A1 | 10/2011 | Henderson et al. | |
| 2012/0275671 A1 | 11/2012 | Eichhorn et al. | |
| 2013/0077892 A1 | 3/2013 | Ikeno et al. | |
| 2014/0049634 A1* | 2/2014 | Tafas | H04N 23/66 |
| | | | 348/79 |
| 2014/0294266 A1 | 10/2014 | Eichhorn et al. | |
| 2014/0354859 A1 | 12/2014 | Noyes et al. | |
| 2018/0017773 A1* | 1/2018 | Tomosugi | G06T 5/73 |
| 2018/0292319 A1* | 10/2018 | Battrell | B01L 7/52 |
| 2018/0292638 A1 | 10/2018 | Bredno et al. | |
| 2020/0334814 A1 | 10/2020 | Gholap et al. | |
| 2020/0355903 A1 | 11/2020 | Bredno et al. | |
| 2020/0400930 A1* | 12/2020 | D'Costa | G16H 10/40 |
| 2021/0201536 A1 | 7/2021 | Atchison et al. | |
| 2021/0263055 A1* | 8/2021 | Mitra | G01N 35/00613 |
| 2021/0264595 A1 | 8/2021 | Plesch et al. | |
| 2021/0279611 A1* | 9/2021 | Kapur | G16H 50/20 |
| 2021/0350112 A1* | 11/2021 | Jenoski | G02B 21/24 |
| 2022/0145236 A1* | 5/2022 | Gau | G01N 27/3275 |
| 2022/0260825 A1 | 8/2022 | Grunkin et al. | |
| 2023/0117821 A1* | 4/2023 | Ivie | G06V 20/698 |
| | | | 382/128 |
| 2023/0206416 A1 | 6/2023 | Maier et al. | |
| 2023/0377154 A1 | 11/2023 | Cheng et al. | |

* cited by examiner

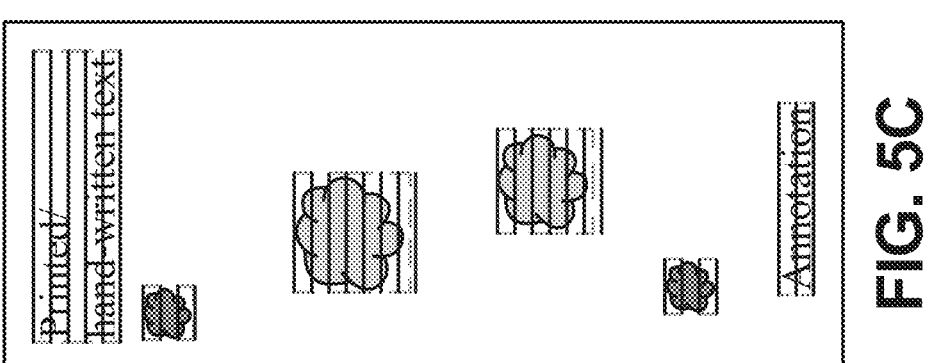
FIG. 5C
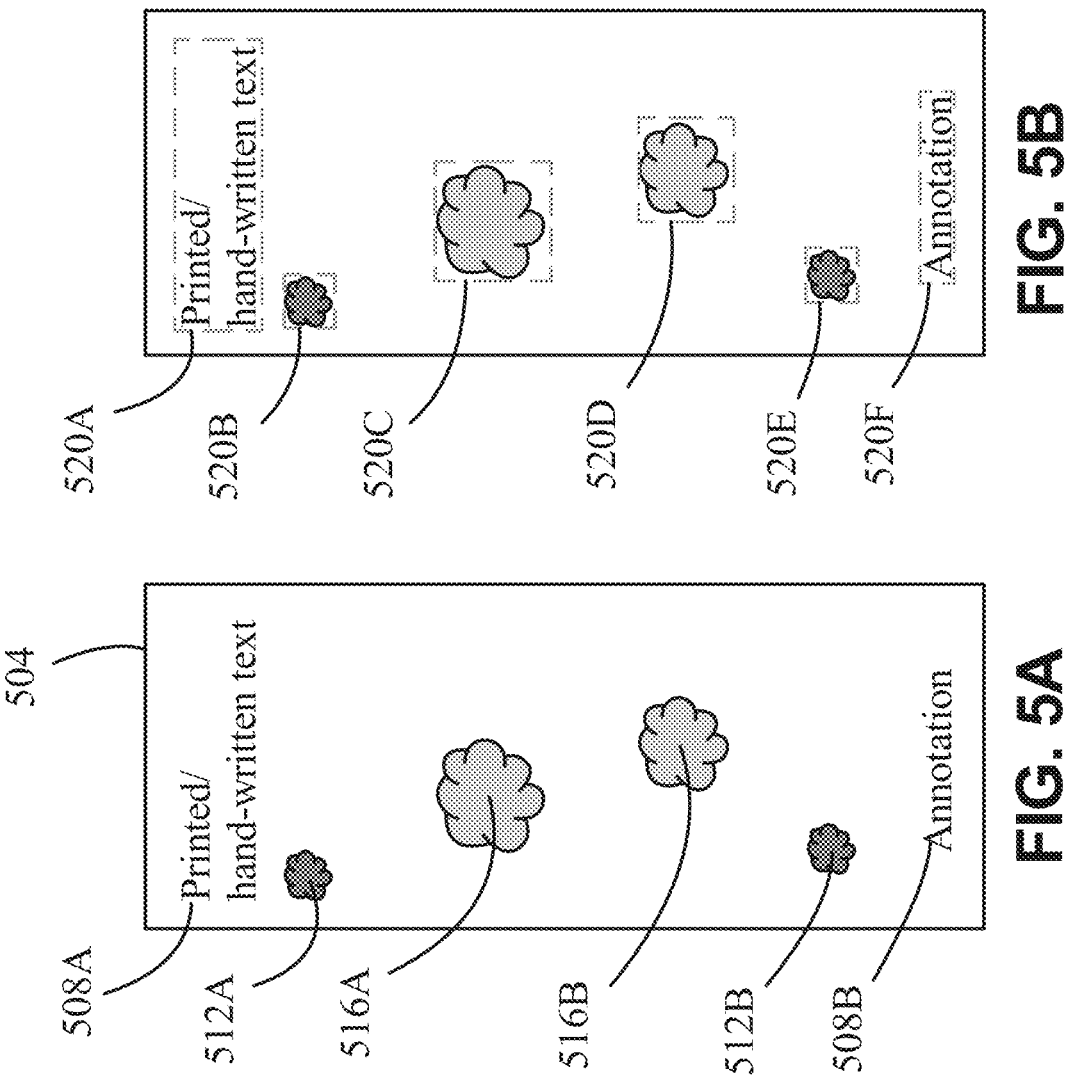
FIG. 5B
FIG. 5A

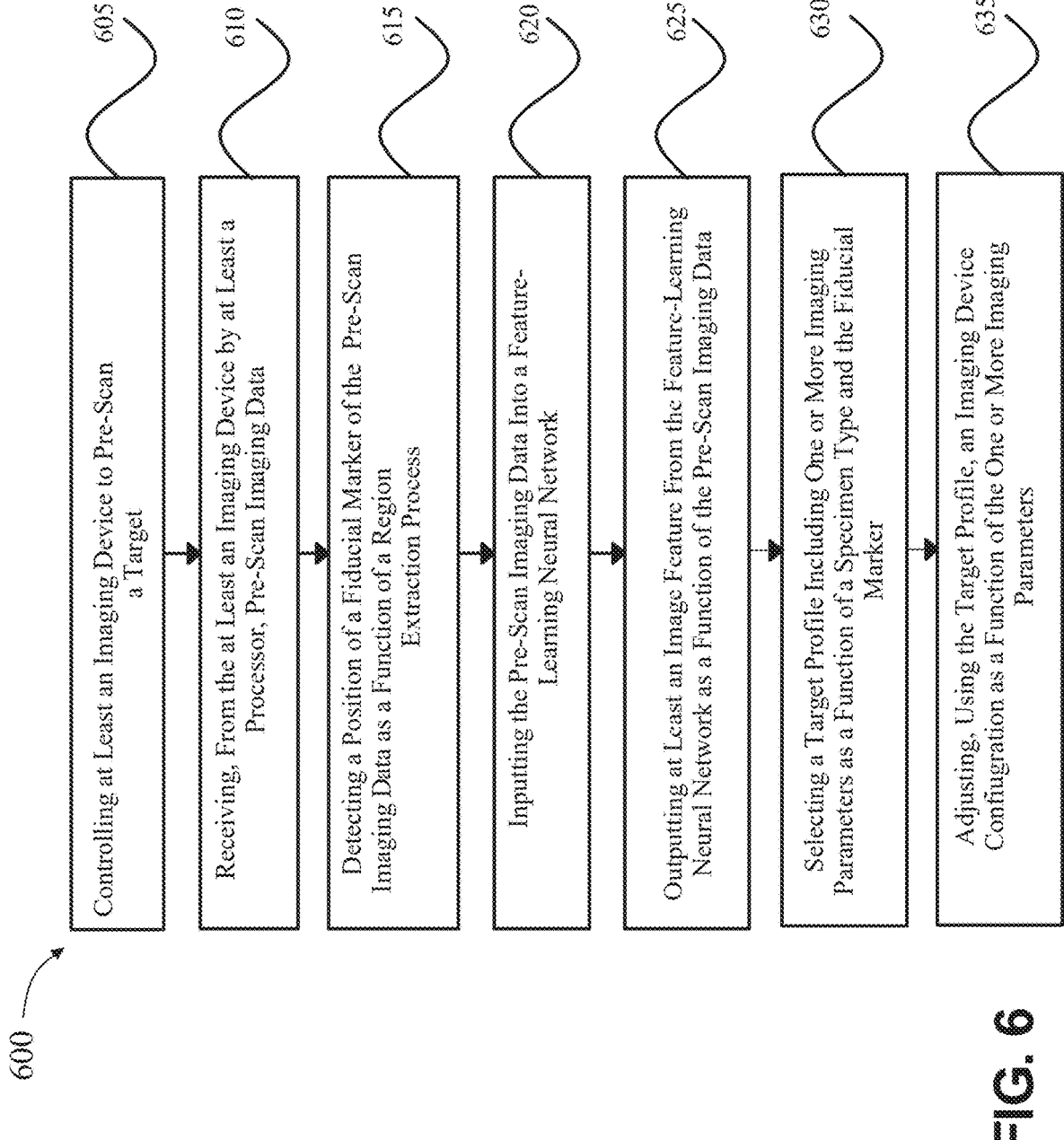

605 — Controlling at Least an Imaging Device to Pre-Scan a Target

610 — Receiving, From the at Least an Imaging Device by at Least a Processor, Pre-Scan Imaging Data 615 — Detecting a Position of a Fiducial Marker of the Pre-Scan Imaging Data as a Function of a Region Extraction Process 620 — Inputting the Pre-Scan Imaging Data Into a Feature-Learning Neural Network 625 — Outputting at Least an Image Feature From the Feature-Learning Neural Network as a Function of the Pre-Scan Imaging Data 630 — Selecting a Target Profile Including One or More Imaging Parameters as a Function of a Specimen Type and the Fiducial Marker 635 — Adjusting, Using the Target Profile, an Imaging Device Configuration as a Function of the One or More Imaging Parameters

SYSTEMS AND METHODS FOR AUTOMATED PROFILE IDENTIFICATION

FIELD OF THE INVENTION

The present invention generally relates to the field of digital pathology. In particular, the present invention is directed to systems and methods for automated profile identification.

BACKGROUND

In digital pathology, precise slide scanning relies on accurately identifying the specimen type and tailoring scan parameters accordingly. Currently, users manually select slide profiles, which can lead to errors when the wrong profile is chosen, potentially causing the scanner to capture irrelevant areas or overlook vital sample regions. Moreover, slides often feature fiducial markers, handwritten annotations, paint markings, or pre-etched placement guides designed to aid in specimen positioning. However, existing systems do not fully utilize these markers to automate slide identification and streamline scanning workflows.

SUMMARY OF THE DISCLOSURE

In an aspect, a system for automated profile identification may include at least an imaging device configured to pre-scan a target to generate pre-scan imaging data, wherein the target includes a fiducial marker and a computing device. Wherein the computing device includes at least a processor and a memory communicatively connected to the at least a processor and containing instructions configuring the at least a processor to control the at least an imaging device while pre-scanning the target, receive, from the at least an imaging device, the pre-scan imaging data, detect a position of the fiducial marker within the pre-scan imaging data, input the pre-scan imaging data into a feature-learning neural network, output at least an image feature from the feature-learning neural network as a function of the pre-scan imaging data, wherein the at least a feature represents at least a specimen type, select a target profile as a function of the specimen type and the fiducial marker, wherein the target profile includes one or more imaging parameters, and adjust, using the target profile, one or more imaging device parameters as a function of the one or more imaging parameters.

In another aspect, a method for automated profile identification may include controlling the at least an imaging device while pre-scanning the target, receiving, from the at least an imaging device, the pre-scan imaging data, detecting a position of the fiducial marker within the pre-scan imaging data, inputting the pre-scan imaging data into a feature-learning neural network, outputting at least an image feature from the feature-learning neural network as a function of the pre-scan imaging data, wherein the at least a feature represents at least a specimen type, selecting a target profile as a function of the specimen type and the fiducial marker, wherein the target profile includes one or more imaging parameters, and adjusting, using the target profile, one or more imaging device parameters as a function of the one or more imaging parameters.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 5A-5C are diagrams depicting a slide including various features, identifications of regions of interest, and scanning of rows within the regions of interest;

FIG. 6 is a flow diagram depicting an exemplary embodiment of a method for automated profile identification.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for automated profile identification. In an embodiment, the system may include at least an imaging device and a computing device that includes a processor and memory, wherein the processor is configured to pre-scan a target, detect fiducial markers using a region extraction process, profile the detected markers using a classification model, and select a target profile comprising one or more imaging parameters.

Aspects of the present disclosure can be used to optimize the digital scanning process in pathology by automatically identifying specimen types and adjusting imaging parameters to ensure complete and accurate image capture. Aspects of the present disclosure can also be used to enhance workflow efficiency by integrating inline validation and automated feedback mechanisms to dynamically refine the scanning process. This is so, at least in part, because the system may leverage machine-learning models trained on diverse specimen datasets to detect fiducial markers, determine optimal imaging modes and focus strategies, and implement real-time corrections based on high magnification feedback.

Aspects of the present disclosure allow for improved diagnostic accuracy and streamlined laboratory operations by reducing manual intervention and minimizing scanning errors. Exemplary embodiments illustrating aspects of the present disclosure are described below in the context of several specific examples.

Figure 1:
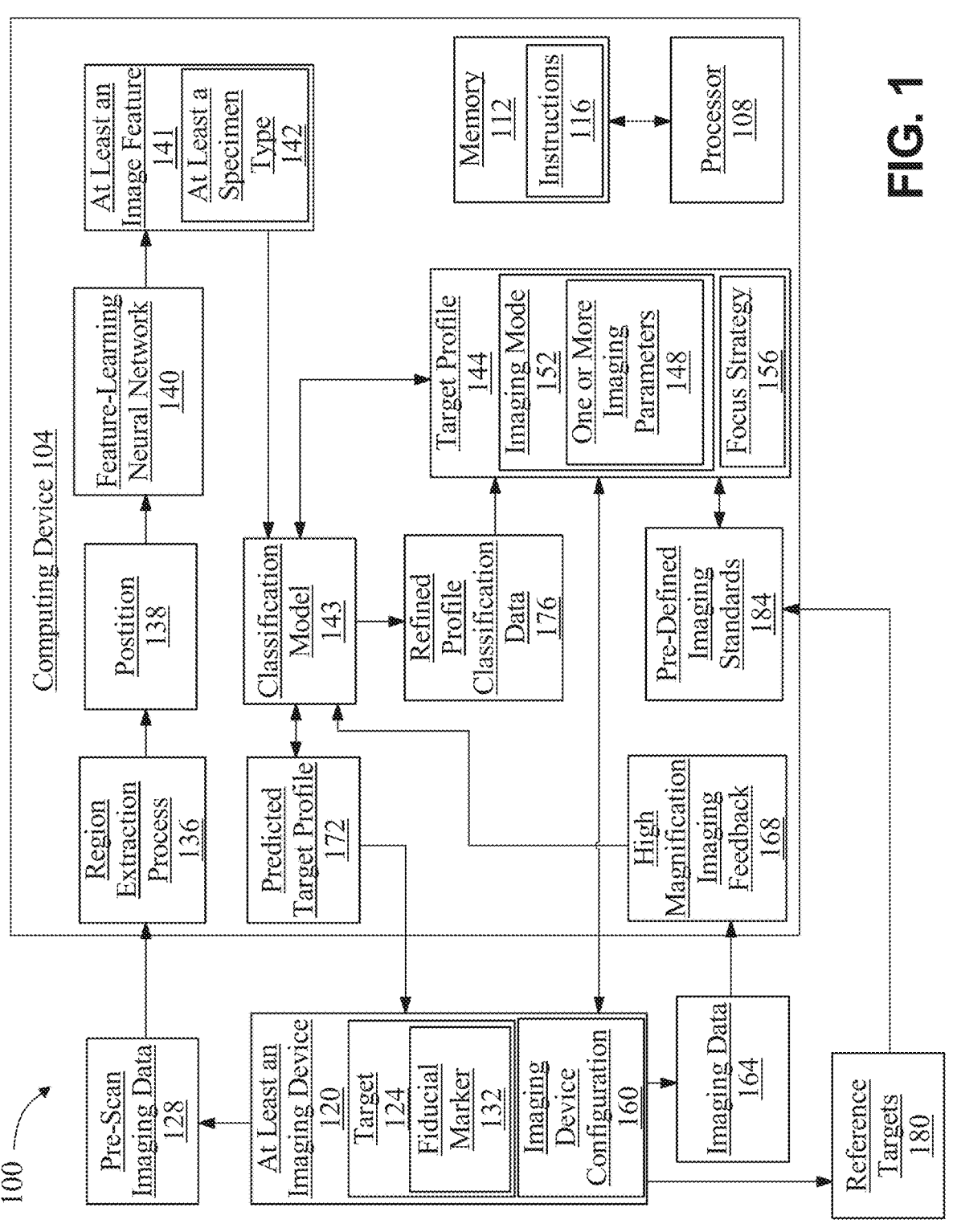
FIG. 1 is a block diagram of an exemplary system for automated profile identification.

Referring now to FIG. 1, an exemplary embodiment of a system 100 for automated profile identification is illustrated. In an embodiment, system 100 includes at least an imaging device 120 configured to pre-scan a target to generate pre-scan imaging data, wherein a slide includes a fiducial marker 132. For purposes of this disclosure, an "imaging device" is a tool that captures, records, or processes visual information into an image. At least an imaging device 120 may convert optical signals into electronic data, which can then be displayed, stored, or further processed. At least an imaging device 120 may include, for example, digital cameras, scanners, and/or other medical imaging equipment such as X-ray machines and MRI scanners. In one embodiment, at least an imaging device 120 may be configured to capture optical information from slide specimens using various modalities. In such an embodiment, at least an imaging device 120 may play a pivotal role in the automated identification of slide specimens. High-resolution images produced by at least an imaging device 120 may be processed by one or more pattern recognition algorithms or artificial intelligence modules, which detect and classify features pertinent to the specimen. By automating the identification process, system 100 may minimize reliance on manual interpretation and enhance overall diagnostic efficiency.

Furthermore, at least an imaging device 120 may be employed to localize regions of interest on the slide specimen. Localization may ensure that specific areas, which may exhibit diagnostically relevant features, are accurately identified and subsequently targeted for detailed scanning. This targeted approach may optimize the scanning workflow by directing resources to the most critical areas of the specimen, thereby reducing processing time and improving the accuracy of the diagnostic output. Additionally, imaging data 164 generated by the imaging device may be stored in a digital format and subsequently processed using advanced software applications, including machine learning algorithms. Such processing facilitates the enhancement of image quality, the extraction of further diagnostic information, and the potential for integration into broader healthcare data management systems.

With continued reference to FIG. 1, in an embodiment, at least an imaging device 120 may include one or more sensors for capturing image signals representative of an image of a scene (e.g., a scene including a specimen). For instance, and without limitation, a sensor may include a light sensor, image sensor, focal plane array, and the like. In various embodiments, sensors may provide for representing and/or converting a captured image signal of a scene to digital data. For instance, and without limitation, sensors may include an analog-to-digital converter. In one or more embodiments, at least a processor 108 may be adapted to receive image signals from at least an imaging device 120 (e.g., image sensor), process image signals to provide processed image data, store image signals and/or image data in memory 112, and/or retrieve stored image signals and/or image data from memory 112 (e.g., for compilation or combinations as discussed further in this disclosure). In one or more embodiments, at least a processor 108 may be configured to process image signals stored in memory 112 to provide image data to display for viewing by a user and/or operator.

In further reference to FIG. 1, in one or more embodiments, at least an imaging device 120 may include and/or be communicatively connected to a display. In one or more embodiments, display may be configured to display imaging data 164 and any other information described in this disclosure, such as annotations or text. In one or more embodiments, at least a processor 108 may be configured to retrieve imaging data 164 and information from memory 112 and display such image data and information on display. In other embodiments, display may receive imaging data 164 directly from an optical system.

Still referring to FIG. 1, in some embodiments, at least an imaging device 120 may include at least an optical system. As used in this disclosure, an "optical system" is an arrangement of one or more components which together act upon or employ electromagnetic radiation, such as light (e.g., visible light, infrared light, UV light, or the like). The optical system may include one or more optical elements, including without limitation lenses, mirrors, windows, filters, and the like. In an embodiment, the optical system may form an optical image that corresponds to an optical object. For instance, and without limitation, optical system may form an optical image at or upon an optical sensor, which can capture, e.g., digitize, the optical image. In some cases, optical system may have at least a magnification. For instance, and without limitation, optical system may include an objective (e.g., microscope objective) and one or more reimaging optical elements that together produce an optical magnification. In some cases, a degree of optical magnification may be referred to herein as zoom. As used herein, an "optical sensor" is a device that measures light and converts the measured light into one or more signals; one or more signals may include, without limitation, one or more electrical signals. In some embodiments, optical sensors may include at least a photodetector. As used herein, a "photodetector" is a device that is sensitive to light and thereby able to detect light. In some embodiments, a photodetector may include a photodiode, a photoresistor, a photosensor, a photovoltaic chip, and the like. In some embodiments, optical sensors may include a plurality of photodetectors. Optical sensor may include, without limitation, a camera. Optical sensor may be in electronic communication with at least a processor 108. As used herein, "electronic communication" as used in this disclosure is a shared data connection between two or more devices. In some embodiments, at least an imaging device 120 may include two or more optical sensors.

With further reference to FIG. 1, in some embodiments, optical system may include a camera. In some cases, a camera may include one or more optics. Exemplary non-limiting optics include spherical lenses, aspherical lenses, reflectors, polarizers, filters, windows, aperture stops, and the like. In some embodiments, one or more optics associated with a camera may be adjusted in order to, in non-limiting examples, change the zoom, depth of field, and/or focus distance of the camera. In some embodiments, one or more of such settings may be configured to detect a feature of a sample on a slide. In some embodiments, one or more of such settings may be configured based on a parameter set, as described below. In some embodiments, camera May capture images at a low depth of field. In a non-limiting example, camera may capture images such that a first depth of sample is in focus and a second depth of sample is out of focus. In some embodiments, an autofocus mechanism may be used to determine focus distance. In some embodiments, focus distance may be set by parameter set. In some embodiments, camera may be configured to capture a plurality of images at different focus distances. In a non-limiting example, camera may capture a plurality of images at different focus distances, such that images are captured where each focus depth of the sample is in focus in at least one image. In some embodiments, at least a camera may include an image sensor. Exemplary non-limiting image sensors include digital image sensors, such as without limitation charge-coupled device (CCD) sensors and complimentary metal-oxide-semiconductor (CMOS) sensors. In some embodiments, a camera may be sensitive within a non-visible range of electromagnetic radiation, such as without limitation infrared.

In further reference to FIG. 1, in some embodiments, at least an imaging device 120 may include a machine vision system. A machine vision system may include an optical system or may be communicatively connected to an optical system, at least a processor 108, memory 112, and the like. In some embodiments, a machine vision system may include at least a camera. A machine vision system may use images, such as images from at least a camera, to make a determination about a scene, space, and/or object. For example, in some cases a machine vision system may be used for world modeling or registration of objects within a space. In some cases, registration may include image processing, such as without limitation object recognition, feature detection, edge/corner detection, and the like. Non-limiting examples of feature detection may include scale invariant feature transform (SIFT), Canny edge detection, Shi Tomasi corner detection, and the like. In some cases, registration may include one or more transformations to orient a camera frame (or an image or video stream) relative a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z-axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy-plane of a first frame; a result, x and y translational components and φ may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy-plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. In some cases, a machine vision system may use a classifier, such as any classifier described throughout this disclosure. A z-axis, as used in this disclosure, is an axis that is orthogonal to the xy-plane and, thus, a top surface of a slide.

With continued reference to FIG. 1, in an embodiment, at least an imaging device 120 may include one or more slide tables that provide a stable and level surface for positioning slides during an imaging process. These slide tables may be engineered to minimize vibrations and ensure precise alignment of each slide, thereby maintaining image clarity and consistency across multiple scans. In addition to slide tables, at least an imaging device 120 may also incorporate pick baskets that serve as temporary storage for slides prior to and after imaging. These pick baskets may be configured to organize and segregate slides based on their processing status, such as slides queued for imaging, those currently being scanned, and those that have been successfully processed. The design of the pick baskets may facilitate efficient workflow management, reducing the risk of misplacement or mix-ups, and allows the system to quickly retrieve and reposition slides as needed. Moreover, at least an imaging device 120 may further include an automated slide feeder that interfaces with the slide tables and pick baskets. This component may be responsible for transferring slides from the pick basket onto the slide tables in a controlled manner, ensuring that each slide is properly oriented and aligned for optimal imaging. The integration of these physical components may enhance the overall throughput and reliability of at least an imaging device 120, enabling continuous operation with minimal manual intervention. These physical elements may work in tandem with at least an imaging device's 120 control systems and dedicated processing units, ensuring that adjustments to imaging parameters, such as exposure time, sensor gain, and illumination intensity, are seamlessly synchronized with the physical handling of the slides. As a result, at least an imaging device not only captures high-quality digital images of each slide but may also maintain a robust, automated workflow that minimizes human error and maximizes operational efficiency.

In continued reference to FIG. 1, in an embodiment, at least an imaging device 120 may include a plurality of imaging devices configured to simultaneously capture imaging data 164 of a plurality of targets 124. For example, rather than relying on a single device to sequentially capture images from each target 124, multiple imaging devices may operate concurrently, each dedicated to acquiring data from a specific target 124. This parallel processing may significantly enhance system's 100 throughput and operational efficiency, especially in environments where multiple specimens or regions of interest must be analyzed concurrently. Moreover, the plurality of imaging devices may be arranged such that each device is optimized for a particular imaging modality or target 124 type. In one instance, one imaging device might be designed to capture high-resolution color images, while another captures fluorescent or infrared images, thereby enabling multi-modal analysis. This simultaneous capture approach not only expedites the imaging process but may also allow for the fusion of data from different modalities to create a more comprehensive diagnostic picture. Additionally, integrating multiple imaging devices may facilitate the synchronization and alignment of images through a central processing unit. The central unit can coordinate image acquisition so that the data from each device is captured under consistent conditions, ensuring that the resulting images are both time-aligned and spatially registered. This may be particularly beneficial when the captured data is used for further processing, such as pattern recognition, image enhancement, or diagnostic evaluations. Furthermore, the use of a plurality of imaging devices may provide redundancy, thereby increasing the reliability of the overall system. Should one device encounter a malfunction or produce suboptimal images, the remaining devices may still ensure that adequate data is captured for accurate analysis. This redundancy can be critical in high-stakes diagnostic settings, where the timely and accurate capture of imaging data 164 is essential.

In continued reference to FIG. 1, in an embodiment, system 100 includes a computing device 104. Computing device 104 includes at least a processor 108 communicatively connected to a memory 112. Wherein memory 112 contains instructions 116 configuring at least a processor 108 to undergo methods as described herein. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof.

Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices, computing device 104 may be implemented, as a non-limiting example, using a "shared nothing" architecture.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With further reference to FIG. 1, in an embodiment, at least a processor 108 is configured to control at least an imaging device 120 while pre-scanning target 124. For purposes of this disclosure, a "pre-scan" refers to an initial imaging step performed before a full or high-resolution scan. During the pre-scan, system 100 may capture pre-scan imaging data 128, in some cases, at a lower resolution, a lower magnification, or with different imaging parameters, to quickly assess and identify areas of interest within a specimen or field of view. Higher magnification scans may take longer and use more resources than a lower magnification or lower resolution scan; system 100 benefits from the ability to locate where and what type of specimen is present on a given slide configuring imaging device 120 to efficiently complete high magnification scans. The pre-scan may serve multiple purposes. It may be used to locate specific targets 124 or regions that require more detailed analysis, to verify the presence and position 138 of the specimen, or to guide subsequent scan operations by determining optimal scanning parameters. By obtaining a rapid overview of the target 124 area, pre-scan helps ensure that the subsequent high-resolution or focused scanning operations are both efficient and accurate, reducing overall processing time and resource consumption.

In continued reference to FIG. 1, for purposes of this disclosure, a "target" refers to a region, object, or area of interest within a specimen or field of view that is identified for subsequent detailed analysis or imaging. For example, and without limitation, target 124 may represent a specific structure, feature, or anomaly that is deemed diagnostically or scientifically significant. Alternatively, target 124 may include a fiducial marker 132. For purposes of this disclosure, a "fiducial marker" is a reference element integrated into a specimen or imaging environment that serves as a fixed, identifiable point for calibration, alignment, or spatial registration. For example, and without limitation, fiducial marker 132 may include printed markers, paint marks, crosshairs, handwritten labels, and/or pre-etched regions to infer specimen positioning 138 and at least a specimen type 142. The fiducial marker 132 may be designed to have distinct, easily recognizable features, such as a specific shape, pattern, or color, that can be reliably detected by at least a processor 108. The use of fiducial markers 132 may enable accurate alignment and scaling of images, ensuring that spatial relationships within the captured imaging data 164 are maintained. This may be particularly important in applications where precise image stitching, overlay, or quantitative analysis is required. By providing a consistent reference point, fiducial markers 132 help correct variations in positioning, orientation, or distortion during imaging procedures. Continuing, target 124 may be identified during an initial imaging step, such as a pre-scan, which provides a preliminary overview of the specimen. Once target 124 is identified, system 100 can direct high-resolution or focused scanning efforts to a particular area, thereby optimizing resource usage and enhancing diagnostic accuracy.

With further reference to FIG. 1, in an embodiment, at least a processor 108 is configured to receive, from at least an imaging device 120, pre-scan imaging data 128. In an embodiment, pre-scan imaging data 128 may include an initial set of images captured under lower resolution or alternative imaging parameters, which may provide a rapid overview of the specimen or field of view. This preliminary data may enable at least a processor 108 to quickly assess the general layout and key features within target 124 area. Upon receiving pre-scan imaging data 128, at least a processor 108 may execute a series of analytical algorithms to identify regions of interest, detect anomalies, or determine specific targets 124 for further detailed scanning. At least a processor's 108 analysis of this data can inform decisions regarding subsequent imaging parameters, such as adjusting resolution, focus, or exposure settings, thereby optimizing the overall scan workflow. Additionally, at least a processor 108 may utilize pre-scan data to calibrate and align subsequent high-resolution scans. By comparing the preliminary images with known fiducial markers 132 or calibration patterns, at least a processor 108 can accurately map the spatial relationships within the specimen, ensuring that detailed scans are correctly registered and aligned with the pre-scan overview.

With further reference to FIG. 1, in an embodiment, at least a processor 108 is configured to detect a position 138 of fiducial marker 132 within pre-scan imaging data 128. In an embodiment, detecting the position 138 of fiducial marker 132 may include performing a region extraction process. For purposes of this disclosure, a "region extraction process" is a procedure designed to identify and isolate specific regions of interest within an image. In an embodiment, a region extraction process 136 may begin with the reception of pre-scan imaging data 128, such as a pre-scan or full-resolution image, which contains a broader view of the specimen or scene. A region extraction process 136 may involve several steps, starting with preprocessing the image to enhance features such as contrast or edge definition. Following one or more preprocessing steps, segmentation algorithms may be applied to differentiate distinct areas based on various criteria, such as intensity, color, texture, or shape. These algorithms may work to delineate boundaries between different regions, effectively partitioning the image into segments.

Still referring to FIG. 1, in some embodiments, at least an imaging device 120 may include a machine vision system that includes at least a camera. A machine vision system may use images from at least a camera, to make a determination about a scene, space, and/or object. For example, in some cases a machine vision system may be used for world modeling or registration of objects within a space. In some cases, registration may include image processing, such as object recognition, feature detection, edge/corner detection, and the like. Non-limiting examples of feature detection may include scale invariant feature transform (SIFT), Canny edge detection, Shi Tomasi corner detection, and the like. In some cases, registration may include one or more transformations to orient a camera frame (or an image or video stream) relative to a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy plane of a first frame; a result, x and y translational components and ø may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. In some cases, a machine vision system may use a classifier, such as any classifier described throughout this disclosure.

With further reference to FIG. 1, in an embodiment, image segmentation as described herein may be consistent with one or more aspects of image segmentation and methods thereof as described in U.S. Pat. No. 11,978,185, filed on Nov. 17, 2023, entitled "SYSTEMS AND METHODS FOR COLOR GAMUT NORMALIZATION FOR PATHOLOGY SLIDES," which is incorporated by reference herein in its entirety.

In further reference to FIG. 1, in an embodiment, once segmentation is complete, at least a processor 108 may extract the regions that are deemed significant based on pre-established parameters or learned features. These criteria may be pre-established parameters that have been defined based on prior domain knowledge or regulatory requirements. For example, parameters such as minimum size, shape, color intensity, or contrast thresholds might be applied to exclude regions that do not meet a certain standard of relevance. This filtering process may ensure that only the most promising areas are carried forward for further analysis. In addition to fixed parameters, system 100 may also utilize learned features derived from machine learning models or statistical analyses. In such cases, the system may have been trained on a dataset, for example, an image repository, to recognize specific patterns or characteristics that are indicative of regions of interest. These learned features might include complex attributes such as texture, spatial relationships, or morphological details that are not easily captured by simple threshold-based rules. As a result, at least a processor 108 can dynamically adapt to variations in image quality or specimen type, making the extraction process more robust and accurate. These extracted regions, often referred to as regions of interest (ROIs), can then be further analyzed or processed by subsequent components of system 100. This targeted extraction may enable more efficient and accurate analysis by focusing computational resources on the most relevant portions of the image.

Having isolated the most relevant regions of interest through dynamic adaptation and targeted extraction, system 100 may be poised for further data extraction and analysis. In particular, once these key regions are identified, additional processing techniques can be applied to extract specific information embedded within them, such as textual content. This integration of region extraction with text recognition capabilities enables system 100 to convert visual data into machine-readable formats, thereby broadening the scope of analysis and supporting functionalities like keyword detection and document indexing. For example, system 100 may extract textual information from a label or marker of the slide.

In continued reference to FIG. 1, in an embodiment, feature-learning neural network 140 may be employed to determine target's 124 location as a function of fiducial marker 132. Feature-learning neural network 140 may be trained using a supervised learning approach on a dataset containing images annotated with both fiducial marker positions and corresponding target coordinates. The architecture of feature-learning neural network 140 may include an initial series of convolutional layers for hierarchical feature extraction, which enable the identification of salient image regions corresponding to fiducial markers. The extracted features may be processed by subsequent layers, including a regression head that predicts fiducial marker's 132 position within an image coordinate system. Integrated within the network may be a spatial transformation module that leverages the learned positional relationship between fiducial marker 132 and target 124. This module may apply a learned transformation, parameterized by weights derived during training, to map the detected fiducial position to the target's coordinates. In embodiments where multiple fiducial markers 132 are present, feature-learning network 140 may aggregate the predictions from different regions using mechanisms such as attention or weighted averaging, thereby enhancing the robustness and accuracy of the target 124 localization. The integrated design may allow feature-learning neural network 140 to adaptively compensate for variations in imaging conditions, distortions, or environmental factors by dynamically learning the spatial dependencies between the fiducial markers 132 and the target 124.

Still referring to FIG. 1, in some embodiments, text recognition capabilities may include optical character recognition or optical character reader (OCR). In an embodiment, at least a processor 108 may be configured to extract data from target 124 using OCR. In some cases, target may include a slide label, and the extracted data may be used to select target profile 144. OCR may include automatic conversion of images of written (e.g., typed, handwritten or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases, a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

Still referring to FIG. 1, in some embodiments an OCR process will include an OCR algorithm. Exemplary OCR algorithms include matrix matching processes and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted features can be compared with an abstract vector-like representation of a character, which might reduce to one or more glyph prototypes. General techniques of feature detection in computer vision are applicable to this type of OCR. In some embodiments, machine-learning processes like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 2-4. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIGS. 2-4.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make us of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

In continued reference to FIG. 1, in some embodiments still, system 100 may be configured to read a barcode. In such an embodiment, at least an imaging device 120 may capture barcode images as part of the overall specimen imaging process. At least a processor 108 may then employ dedicated barcode recognition algorithms that analyze captured imaging data 164 to identify and decode barcode symbols, whether one-dimensional (1D) linear barcodes or two-dimensional (2D) barcodes, embedded on the specimen or its associated documentation. Once the barcode is successfully read, the decoded data may be converted into a machine-readable format and cross-referenced with corresponding specimen records in a database. This integration of barcode reading into the feature recognition process not only streamlines specimen tracking and data association but may also enhance workflow efficiency by automating data entry and reducing manual errors. Additionally, the system may include calibration steps that optimize image capture settings for barcode clarity, ensuring robust performance even in varying imaging conditions.

With further reference to FIG. 1, in an embodiment, system 100 may cross-reference barcode information with corresponding specimen or slide records in a database. This integration may ensure that each specimen is accurately tracked, and the correct digital records are associated with the physical slides. The use of barcode recognition not only streamlines the specimen tracking process but may also enhance workflow efficiency by automating data entry and reducing the potential for manual errors. In addition to barcode recognition, system 100 can further enhance its functionality by retrieving slide metadata using the barcode or another identifier extracted from the specimen's label through OCR. The barcode or OCR-extracted ID can serve as a unique key that queries a database containing detailed metadata about the slide. This metadata may include information such as the specimen's type, preparation date, staining method, and patient details, among other attributes. Automatically linking this metadata with the captured image data may further improve data accuracy and traceability. In an embodiment, to ensure reliable performance, even in varying imaging conditions, system 100 may include calibration steps that optimize image capture settings specifically for barcode clarity. These calibration processes may adjust parameters like lighting, focus, and exposure to ensure that barcodes and OCR labels are captured with high fidelity. This proactive approach may not only enhance system's 100 ability to accurately decode barcodes and extract metadata but also reduces the risk of errors, ultimately providing a robust audit trail for quality control and troubleshooting.

With further reference to FIG. 1, in an embodiment, at least a processor 108 is configured to input pre-scan imaging data 128 into a feature-learning neural network 140. In an embodiment, feature-learning neural network 140 may include a feature-learning capabilities located at one or more internal nodes.

In further reference to FIG. 1, in an embodiment feature-learning neural network 140 may utilize feature learning algorithms to detect co-occurrences in imaging data 164, such as fiducial marker 132. A "feature learning algorithm," as used herein, is a machine-learning algorithm that identifies associations between elements of data in a data set, which may include without limitation a training data set, where particular outputs and/or inputs are not specified. For instance, without limitation, a feature learning algorithm may detect co-occurrences of elements of data, as defined above, with each other. As a non-limiting example, feature learning algorithms may detect co-occurrences of elements, as defined above, with each other. Computing device may perform a feature learning algorithm by dividing elements or sets of data into various sub-combinations of such data to create new elements of data and evaluate which elements of data tend to co-occur with which other elements. In an embodiment, a first feature learning algorithm may perform clustering of data.

Continuing to refer to FIG. 1, a feature learning and/or clustering algorithm may be implemented, as a non-limiting example, using a k-means clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster; for instance, and without limitation, a fuzzy clustering algorithm may be used to identify clustering of elements of a first type or category with elements of a second type or category, and vice versa. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, computing device may generate a k-means clustering algorithm receiving unclassified data and outputs a definite number of classified data entry clusters wherein the data entry clusters each contain cluster data entries. K-means algorithm may select a specific number of groups or clusters to output, identified by a variable "k." Generating a k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm may act to identify clusters of closely related data, which may be provided with user cohort labels; this may, for instance, generate an initial set of user cohort labels from an initial set of data, and may also, upon subsequent iterations, identify new clusters to be provided new labels, to which additional data may be classified, or to which previously used data may be reclassified.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids $c_i$ of centroids in set C. Unclassified data may be assigned to a cluster based on $\llbracket \; argmin \rrbracket \_(c_i \ni C) \; dist \; (c_i, x) \rrbracket \hat{} 2$, where argmin includes argument of the minimum, $c_i$ includes a collection of centroids in a set C, and dist includes standard Euclidean distance. K-means clustering module may then recompute centroids by taking mean of all cluster data entries assigned to a centroid's cluster. This may be calculated based on $c_i = 1/|S_i| \Sigma \llbracket \; x_i \ni S_i \rrbracket \hat{} (x_i)$. K-means clustering algorithm may continue to repeat these calculations until a stopping criterion has been satisfied such as when cluster data entries do not change clusters, the sum of the distances have been minimized, and/or some maximum number of iterations has been reached.

Still referring to FIG. 1, k-means clustering algorithm may be configured to calculate a degree of similarity index value. A "degree of similarity index value" as used in this disclosure, includes a distance measurement indicating a measurement between each data entry cluster generated by k-means clustering algorithm and a selected element. Degree of similarity index value may indicate how close a particular combination of elements is to being classified by k-means algorithm to a particular cluster. K-means clustering algorithm may evaluate the distances of the combination of elements to the k-number of clusters output by k-means clustering algorithm. Short distances between an element of data and a cluster may indicate a higher degree of similarity between the element of data and a particular cluster. Longer distances between an element and a cluster may indicate a lower degree of similarity between a elements to be compared and/or clustered and a particular cluster.

With continued reference to FIG. 1, k-means clustering algorithm selects a classified data entry cluster as a function of the degree of similarity index value. In an embodiment, k-means clustering algorithm may select a classified data entry cluster with the smallest degree of similarity index value indicating a high degree of similarity between an element and the data entry cluster. Alternatively, or additionally k-means clustering algorithm may select a plurality of clusters having low degree of similarity index values to elements to be compared and/or clustered thereto, indicative of greater degrees of similarity. Degree of similarity index values may be compared to a threshold number indicating a minimal degree of relatedness suitable for inclusion of a set of element data in a cluster, where degree of similarity indices a-n falling under the threshold number may be included as indicative of high degrees of relatedness. The above-described illustration of feature learning using k-means clustering is included for illustrative purposes only and should not be construed as limiting potential implementation of feature learning algorithms; persons skilled in the art, upon reviewing the entirety of this disclosure, will be aware of various additional or alternative feature learning approaches that may be used consistently with this disclosure.

In further reference to FIG. 1, in an embodiment, at least a processor 108 is configured to output at least an image feature 141 from the feature-learning neural network 140 as a function of pre-scan imaging data 128, wherein at least an image feature 141 represents at least a specimen type 142. For purposes of this disclosure, an "image feature" is an attribute or property extracted from an image for identifying patterns, objects, or regions of interest. In an embodiment, at least an image feature 141 may include edges, corners, and colors, or more complex features, such as textures, shapes, and patterns derived from combinations of simpler elements. At least an image feature 141 may be combined with other image features 141 to indicate or represent a whole, such as at least a specimen type 142. For purposes of this disclosure, "specimen type" refers to the classification of the biological sample that is mounted on a slide for imaging. At least a specimen type 142 may include details such as the tissue of origin (e.g., breast, liver, skin), the nature of the sample (e.g., biopsy, surgical resection, cytology smear), and/or the preparation method (e.g., stained, frozen, or fixed). Understanding at least a specimen type 142 may be critical because it influences the choice of imaging parameters, the interpretation of the captured image, and the subsequent diagnostic or research processes. For instance, different specimen types may require specific staining techniques or imaging modalities to highlight relevant cellular structures or pathological features.

With further reference to FIG. 1, in an embodiment, at least a processor 108 is configured to select a target profile 144 as a function of specimen type and fiducial marker 132, wherein target profile 124 includes one or more imaging parameters 148. For purposes of this disclosure, a "target profile" is defined as a set of one or more imaging parameters and associated data that characterize the desired imaging conditions associated with a fiducial marker and specimen type. For purposes of this disclosure, "one or more imaging parameters" refers to a set of controllable attributes and settings that influence the acquisition, quality, and processing of imaging data 164. One or more imaging parameters 148 may optionally include, but are not limited to, exposure time, gain, focus, resolution, contrast, brightness, white balance, dynamic range, and spatial calibration metrics. In some embodiments, these parameters may be adjusted based on the target profile 144 to optimize imaging conditions and ensure consistent, high-quality image acquisition across various specimen types or fiducial markers 132.

In continued reference to FIG. 1, in an embodiment, target profile 144 may include an imaging mode 152 including one or more imaging parameters 148 selected from a group of resolution, exposure time, illumination intensity, and scanning speed. Further, in an embodiment, imaging mode 152 may be selected as a function of specimen type to optimize image acquisition of target 124. For purposes of this disclosure, an "imaging mode" is defined as a specific configuration of an imaging device that determines the parameters and settings employed during image acquisition and processing. In some embodiments, imaging mode 152 may include predefined settings for attributes such as exposure, focus, resolution, gain, and contrast, which are optimized for capturing images of particular specimens or targets 124. The imaging mode 152 may be automatically selected based on factors such as pre-scan imaging data 128, target profiles 144, or analysis of fiducial markers 132, thereby ensuring that the imaging conditions are tailored to the characteristics of the subject. This approach may enhance consistency and accuracy in subsequent image analysis and processing steps by standardizing the acquisition conditions across varying imaging scenarios.

Still referring to FIG. 1, in an embodiment, target profile 144 may include a focus strategy 156. For purposes of this disclosure, a "focus strategy" is defined as a systematic approach implemented by an imaging system to determine, adjust, and maintain the optimal focal plane during image acquisition. Focus strategy 156 may include, for example, determining an optimal focal plane as a function of target 124 and adjusting focus parameters as a function of the optimal focal plane. In some embodiments, focus strategy 156 may include automated autofocus routines, manual or semi-automated adjustments, and sensor-based feedback mechanisms that collectively analyze pre-scan or live imaging data 164 to ascertain the best focus settings. The focus strategy 156 may consider factors such as specimen morphology, depth of field, illumination conditions, and variations identified via fiducial markers 132 or target profiles 144, with the objective of maximizing image sharpness and quality. This adaptable focus strategy 156 may enhance the precision of captured imaging data 164, thereby supporting subsequent diagnostic or analytical processes.

With continued reference to FIG. 1, in an embodiment, selecting target profile may include using a classification model 143 to classify at least a feature into a target type. In an embodiment, classification model 143 may be trained on a dataset including images of target types, wherein target types include one or more of blood smears, cytology samples, and biopsy samples. In an embodiment, the images of each target type may further be processed to extract relevant features that can be annotated with corresponding target type labels. For instance, images of blood smears may undergo preprocessing to extract features such as cell count, cell morphology, including, for example, shape descriptors like roundness and aspect ratio, and staining intensity metrics. These extracted features may then be labeled with the target type "blood smear." Similarly, images of cytology samples may be analyzed to extract features including nucleus size, cytoplasmic granularity, and boundary irregularities, which may be subsequently labeled as "cytology sample." Likewise, biopsy sample images may have features extracted that reflect tissue architecture patterns, cell density variations, and structural anomalies, with these features being labeled accordingly as "biopsy sample." This integration of specific, feature-based annotations with the target type labels may enable classification model 143 to learn both the raw visual information and the detailed quantitative characteristics of each sample type. Consequently, classification model 143 can achieve enhanced accuracy in distinguishing between different target types during subsequent inference processes. In some embodiments, target types may include one or more of microbiology samples, hematology samples, cytology samples, and histopathology samples. In some embodiments, classification model may be trained on a data set comprising images of target types, such as microbiology samples, hematology samples, cytology samples, and histopathology samples. In some embodiments, hematology samples may be referred to as haematology samples.

In continued reference to FIG. 1, in an embodiment, classification model 143 may include a classifier. In some embodiments, classifier may be trained using a dataset comprising labeled examples and may be configured to process new data, generating a classification output that may be used to inform subsequent processing steps, such as calibration, quality control, or diagnostic evaluation. Classifier may employ supervised, unsupervised, or semi-supervised learning methods, and its parameters may be dynamically updated to enhance classification accuracy over time. For example, classifier may be trained on a dataset including images of various target 124 types, wherein target 124 types include blood smears, cytology samples, and biopsy samples. In some embodiments, the training dataset may be carefully curated to represent the variability inherent in these sample types, capturing differences in staining, morphology, and imaging conditions. Classifier may employ deep learning architectures, such as convolutional neural networks (CNNs), to extract hierarchical features from the images, thereby enhancing its ability to differentiate between the target 124 types based on subtle visual cues. During training, classifier may utilize various preprocessing techniques, such as normalization, augmentation, and noise reduction, to improve its robustness and accuracy. These techniques may enable classifier to generalize across a wide range of image qualities and conditions. Once trained, classifier may be capable of processing new images, accurately categorizing them into the appropriate target 124 types, and thereby facilitating downstream processes such as optimized scanning, diagnostic evaluations, and automated workflow adjustments.

With further reference to FIG. 1, a "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device May generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)÷P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this May be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculating the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

In continued reference to FIG. 1, in an embodiment, at least a processor 108 configured to adjust, using target profile 144, an imaging device configuration 160 imaging device configuration 160 as a function of the one or more imaging parameters 148. In some embodiments, at least a processor 108 may dynamically control various aspects of the imaging device configuration 160 of at least an imaging device 120 based on real-time analysis of imaging data 164 and feedback from system 100 components. For example, at least a processor 108 may adjust parameters such as exposure time, sensor gain, lighting, scan speed, field of view (FOV), z-stack, and illumination intensity to optimize the capture conditions according to a target profile 144 or imaging mode 152. For instance, the exposure time defines the period during which the imaging sensor is active, directly affecting the amount of light collected. Sensor gain controls the amplification of the signal, which is crucial for managing the dynamic range and ensuring that low-light images are adequately captured without saturating brighter areas. Lighting and illumination intensity parameters determine the quality and uniformity of light that reaches the specimen, balancing brightness and contrast to optimize the visibility of key features. Additionally, the scan speed parameter may govern how quickly at least an imaging device 120 acquires sequential images, which may be especially important for high-throughput or time-sensitive applications. The FOV setting controls the spatial dimensions of the captured image, ensuring that the appropriate region of the specimen is within the frame for accurate analysis. The z-stack parameter may involve capturing a series of images at different focal depths, facilitating three-dimensional reconstruction or analysis of specimens with depth variations. Therefore adjustments to the z-stack parameter may include adjusting a distance between the different stacks of the z-stack as a function of an identified specimen.

In continued reference to FIG. 1, in an embodiment, imaging device configuration 160 and methods of adjustment as described herein may be consistent with one or more aspects of imaging device configurations as described in U.S. Pat. No. 11,983,874, filed on Jul. 25, 2023, entitled "IMAGING DEVICE AND A METHOD FOR IMAGE GENERATION OF A SPECIMEN," which is incorporated by reference herein in its entirety.

With further reference to FIG. 1, in an embodiment, these adjustments may be carried out by interfacing with the imaging device's control circuitry or firmware, thereby modifying settings that directly impact the quality and accuracy of the captured image data. Furthermore, at least a processor 108 may utilize a feedback loop wherein preliminary imaging data 128, such as that obtained during a pre-scan, guides the adjustment of imaging parameters. This feedback loop may include analyzing the image quality and comparing it against predefined thresholds or calibration standards, with at least a processor 108 subsequently modifying the imaging device configuration 160 to correct for any deviations. Additionally, at least a processor 108 might implement algorithms that take into account variations detected using fiducial markers 132 or target profiles 144 to further refine imaging conditions. In some embodiments, at least a processor may also be capable of storing these adjusted configurations as part of a dynamic imaging protocol that can be reapplied or further optimized in future imaging sessions, thereby ensuring consistency and enhancing overall system performance.

With continued reference to FIG. 1, in an embodiment, at least an imaging device 120 may be configured to capture imaging data 164 as a function of one or more imaging parameters 148 determined from pre-scan imaging data 128. In such embodiments, at least an imaging device 120 may initially perform a pre-scan to acquire a preliminary set of images, which are then analyzed by at least a processor 108 or dedicated analysis module. This analysis may identify key characteristics, such as brightness, contrast, focus, and noise levels, that inform the selection of optimal imaging parameters for subsequent, higher-resolution or full-scale image acquisition. Based on the results of this analysis, at least a processor 108 may determine one or more imaging parameters 148, which may include adjustments to exposure time, sensor gain, focus settings, illumination intensity, and other configuration settings. These parameters may then be applied to at least an imaging device 120, thereby modifying its operational settings to optimize the capture of imaging data 164. The adjustments may ensure that at least an imaging device 120 is calibrated to the specific conditions observed during the pre-scan, enhancing image quality and ensuring consistency across various specimens or imaging conditions. In some embodiments, this process may be implemented as part of a feedback loop wherein at least an imaging device 120 continuously refines its configuration based on iterative analysis of pre-scan data. This adaptive approach may allow system 100 to compensate for variations in specimen type or imaging environment, leading to more precise and reliable data capture during the main scanning operation.

In further reference to FIG. 1, in an embodiment, at least a processor 108 may be further configured to receive high magnification imaging feedback 168 from at least an imaging device 120. For purposes of this disclosure, "high magnification imaging feedback" is defined as a feedback mechanism by which imaging data 164 captured at high magnification is analyzed and used to adjust or optimize subsequent imaging operations. In some embodiments, high magnification imaging feedback 168 may involve real-time or near real-time processing of high-resolution images to assess parameters such as focus accuracy, resolution, illumination uniformity, and specimen detail. At least a processor 108 or a dedicated analysis module may then use this feedback to automatically adjust imaging parameters or to refine the imaging device configuration 160, thereby ensuring that optimal imaging conditions are maintained. Optionally, high magnification imaging feedback 168 may incorporate iterative adjustments, wherein successive images captured at high magnification are analyzed to detect variations or deviations from desired imaging quality. This information may then be fed back into system 100 to dynamically update parameters such as exposure, focus strategy 156, or illumination settings. Such a mechanism may improve the overall accuracy and consistency of the imaging process, particularly in applications where capturing fine details at high magnification is critical for diagnostic or analytical purposes.

In further referenced to FIG. 1, in an embodiment, at least a processor 108 may be configured to verify and correct a predicted target profile 172 as a function of high magnification imaging feedback 168. In an embodiment, at least a processor 108 may initially establish a predicted target profile 172 based on pre-scan imaging data 128 and ancillary analyses, which may include parameters such as focus, exposure, resolution, and spatial alignment. Subsequently, high magnification imaging feedback 168 may be acquired, providing detailed and high-resolution data that reflects the actual imaging conditions of the target 124 region. At least a processor 108 may then compare the predicted target profile 172 against this high magnification imaging feedback 168 to identify any discrepancies or deviations between the expected and observed imaging parameters. Based on this comparative analysis, at least a processor 108 may optionally be configured to adjust and update the predicted target profile 172 to correct for any identified deviations. For example, if the high magnification feedback indicates suboptimal focus, misalignment, or inconsistent exposure relative to the predicted profile, at least a processor 108 may recalibrate the imaging parameters, such as refining the focus strategy 156, adjusting the exposure settings, or modifying spatial calibration metrics, to align the target profile 144 with the actual imaging conditions. This iterative verification and correction process may ensure that the imaging device configuration 160 remains optimized, thereby enhancing the accuracy and consistency of subsequent imaging operations and downstream diagnostic or analytical procedures.

In continued reference to FIG. 1, in an embodiment, verifying and correcting a predicted target profile 172 as a function of high magnification imaging feedback 168 may include generating refined profile classification data 176 using high magnification imaging feedback 168 and classification model 143. In some embodiments, at least a processor 108 may receive high-resolution images acquired under high magnification conditions and process these images to extract detailed features indicative of the target's 124 characteristics. These features may then be input into a classification model 143, such as a convolutional neural network or other machine-learning framework, which is trained to classify and quantify specific aspects of target 124. The result may include a set of refined profile classification data 176 that more accurately reflects the current imaging conditions and quality parameters of the target 124 region. In an embodiment, refined classification data may serve as a crucial update to the predicted target profile 172 initially derived from pre-scan data and baseline metrics.

With further reference to FIG. 1, in an embodiment, verifying and correcting a predicted target profile 172 as a function of high magnification imaging feedback 168 may include comparing refined profile classification data 176 and predicted target profile 172. In this embodiment, at least a processor 108 may perform a detailed comparison between the refined classification data obtained from high magnification imaging and the previously predicted target profile 172. This comparison may involve assessing deviations in key imaging parameters such as focus accuracy, exposure levels, contrast, and spatial alignment. In an embodiment, system 100 may employ statistical analysis, threshold-based criteria, or machine-learning algorithms to quantify discrepancies between the refined classification data and the predicted values. This comparative analysis may facilitate the identification of any inconsistencies or deviations that might adversely affect the quality or reliability of subsequent imaging or diagnostic processes.

Still referring to FIG. 1, in an embodiment, verifying and correcting a predicted target profile 172 as a function of high magnification imaging feedback 168 may include updating predicted target profile 172 and corresponding one or more imaging parameters 148 as a function of comparing refined profile classification data 176 and predicted target profile 172. In this embodiment, at least a processor 108 may be configured to adjust the predicted target profile 172 by integrating the insights gained from the high magnification imaging feedback 168. Specifically, system 100 may dynamically modify one or more imaging parameters 148, such as exposure time, focus settings, and spatial calibration metrics, to correct for any identified deviations and better align the target profile 144 with the observed imaging conditions. This iterative update process not only refines the target profile 144 but also ensures that subsequent imaging operations are optimized in real time, thereby enhancing the overall accuracy, consistency, and diagnostic reliability of the imaging system.

With continued reference to FIG. 1, for example, in an embodiment involving blood smears, system 100 may generate a predicted target profile 172 based on pre-scan imaging data 128 that includes parameters such as cell distribution, staining intensity, and morphological characteristics of red and white blood cells. High magnification imaging feedback 168 may then be used to capture detailed images of the blood smear, allowing at least a processor 108 to extract refined features such as precise cell boundaries, the presence of abnormal cell shapes, and subtle differences in staining. At least a processor 108 may employ a classification model 143 classifier, trained specifically on blood smear images, to generate refined profile classification data 176. By comparing this refined data to the initially predicted target profile 172, system 100 can adjust imaging parameters, such as focus and exposure settings, to ensure optimal image quality and diagnostic accuracy.

Similarly, in embodiments involving cytology samples, the predicted target profile 172 may be established based on features such as cell clustering patterns, nucleus-to-cytoplasm ratios, and the distribution of cellular anomalies observed during a pre-scan. High magnification imaging feedback 168 may then be utilized to capture detailed views of individual cells and cell clusters, enabling at least a processor 108 to detect fine morphological details and subtle textural differences. Classification model 143 Classifier may process these high-resolution images to generate refined classification data that reflects the true cellular architecture of the cytology sample. At least a processor 108 may then compare refined classification data with the predicted target profile 172 and, if necessary, update the imaging device configuration 160, adjusting parameters like illumination intensity and focus, to enhance the quality of subsequent imaging and analysis.

In the context of biopsy samples, the predicted target profile 172 may include a set of parameters derived from a pre-scan, such as tissue architecture, the presence of distinct structural features (e.g., glandular formations or stromal patterns), and preliminary indications of pathological changes. High magnification imaging feedback 168 may provide a detailed visualization of the biopsy specimen, capturing intricate details such as cellular morphology, intercellular spacing, and tissue organization. In an embodiment, classification model 143 classifier, trained on biopsy images, may process this feedback to produce refined profile classification data 176. By comparing the refined data with the predicted target profile 172, at least a processor 108 may be able to update imaging parameters, such as resolution, contrast, and spatial calibration, to correct any deviations and optimize the imaging conditions. This iterative process may ensure that the biopsy sample is imaged with the highest level of detail and accuracy, which is critical for subsequent diagnostic evaluation and analysis.

With further reference to FIG. 1, in an embodiment, wherein a cytology slide is mistakenly classified as a blood smear during the initial profiling phase, the high magnification imaging feedback 168 may capture detailed features inconsistent with a blood smear. At least a processor 108, upon comparing the refined classification data against the predicted target profile 172, would recognize the discrepancy. Consequently, at least a processor 108 may update the target profile 144 to correctly reflect the cytology slide characteristics and adjust the imaging parameters accordingly. This iterative correction process may ensure that any misclassification is promptly addressed, thereby optimizing the imaging and subsequent diagnostic analysis.

In further reference to FIG. 1, in an embodiment, at least a processor 108 may be further configured to perform inline validation. Wherein, inline validation includes periodically capturing images of reference targets 180 and comparing the images of reference targets 180 against pre-defined imaging standards 184 to verify and maintain accuracy. For purposes of this disclosure, "inline validation" is a process whereby imaging data 164, operational parameters, or processing outputs are concurrently verified and validated during their acquisition or processing. In some embodiments, inline validation may be performed in real time or near-real time, ensuring that the data meets predetermined quality or calibration standards as it is generated. This process may include confirming the accuracy of target profiles 144, imaging parameters, or other extracted features, and may enable prompt detection and correction of deviations or anomalies within the imaging workflow. Inline validation thus may contribute to maintaining the overall integrity and reliability of the imaging system, reducing the need for post-processing corrections and facilitating a more efficient and accurate diagnostic or analytical process.

Still referring to FIG. 1, for purposes of this disclosure, "pre-defined imaging standards" refer to a set of predetermined quality and calibration benchmarks that at least an imaging device 120 is required to meet during operation. These standards may be established prior to the acquisition of imaging data 164 and serve as reference criteria for evaluating the quality and accuracy of the captured images. They may encompass various quality metrics, including resolution, contrast, brightness, signal-to-noise ratio, and uniformity, and may define acceptable ranges or thresholds for each of these parameters. In addition, pre-defined imaging standards 184 may include calibration benchmarks that may be essential for ensuring spatial accuracy, geometric fidelity, and color consistency. For example, reference targets with known dimensions or patterns may be used to verify that system's 100 spatial calibration is accurate, and that any geometric distortion is within acceptable limits. These calibration criteria may be critical for applications where precise measurements and accurate reproductions of the subject matter are required. Pre-defined imaging standards 184 may also establish consistency requirements, ensuring that each image captured during the process adheres to the same quality criteria. This consistency may be particularly important in diagnostic or analytical applications, where even minor deviations can lead to significant errors in interpretation. In an embodiment, pre-defined imaging standards 184 may be designed to facilitate inline validation, wherein imaging data, operational parameters, or processing outputs are concurrently verified and validated during their acquisition or processing. By periodically capturing images of reference targets 180 and comparing them against these pre-defined standards 184, system 100 can detect any deviations or anomalies in real time or near-real time. This prompt detection may allow for immediate corrective actions, reducing the need for extensive post-processing corrections and thereby enhancing the overall efficiency and reliability of the imaging workflow.

With further reference to FIG. 1, in an embodiment, inline validation and quality control as described herein may be consistent with one or more aspects of inline quality control of slide digitization as described in U.S. patent application Ser. No. 18/602,947, filed on Mar. 12, 2024, entitled "SYSTEMS AND METHODS FOR INLINE QUALITY CONTROL OF SLIDE DIGITIZATION," and 1519-030USU1, U.S. Pat. No. 11,997,240, filed on Jul. 27, 2023, entitled "METHOD AND AN APPARATUS FOR INLINE IMAGE SCAN ENRICHMENT," both of which are incorporated by reference herein in their entirety.

With continued reference to FIG. 1, in an embodiment, computing device 104 may further include a workflow management module configured to schedule, monitor, and log scanning operations and provide automated notifications as a function of an imaging process. In such an embodiment, the workflow management module may function as an integrated control system that orchestrates and manages the various tasks and processes involved in image acquisition and processing. In one aspect, the scheduling function of the workflow management module may be configured to determine the optimal timing and sequence of scanning operations. This may be accomplished using a task scheduler that prioritizes imaging tasks based on factors such as specimen type, imaging mode 152, or target profile 144 requirements. The scheduler may dynamically allocate resources, such as processing time and imaging device access, to different scanning operations, ensuring that tasks are executed in an efficient and conflict-free manner. For instance, if multiple specimens require scanning, the scheduler can arrange the scanning sequence to minimize device idle time while maintaining high image quality. In another aspect, the management module may be configured to monitor scanning operations in real time. This monitoring may be implemented using sensors and system logs that capture data on the operational status of at least an imaging device 120, at least a processor 108, and associated peripherals. The management module may, in some embodiments, continuously check parameters such as scan progress, imaging parameter settings (e.g., exposure, focus, resolution), and environmental conditions. This continuous oversight may allow system 100 to detect deviations from expected behavior, such as a loss of focus or a drop in illumination intensity, and trigger corrective actions. Monitoring may involve both hardware-level diagnostics and software-based analytics that compare current performance against baseline metrics defined in the target profile 144.

With further reference to FIG. 1, in an embodiment, the workflow management module may be further configured to log scanning operations. Logging may involve recording detailed information about each imaging task, including start and end times, operational parameters used, errors encountered, and any adjustments made during the scanning process. This logged data may be critical for post-process analysis, quality assurance, and troubleshooting, as it provides a historical record of system 100 performance and enables retrospective analysis to optimize future imaging sessions. Logs may be stored locally on computing device 104 or transmitted to a centralized database for long-term storage and audit. Additionally, the management module may be designed to provide automated notifications as a function of the imaging process. These notifications may be generated in response to specific triggers, such as the completion of a scan, detection of an error, or the need for operator intervention. Automated notifications can be delivered using various channels, including on-screen alerts, emails, or messages sent to a connected mobile device. The notification system may be integrated with the monitoring and logging functions, ensuring that any deviations, anomalies, or process completions are promptly communicated to the relevant stakeholders. This real-time feedback may enable immediate corrective actions and support continuous improvement of the scanning workflow. Overall, the workflow management module may encapsulate the scheduling, monitoring, logging, and notification functions within a unified framework that enhances the efficiency, accuracy, and reliability of the imaging process. By automating these critical aspects of the scanning workflow, computing device 104 may be capable of maintaining optimal operational performance and providing robust support for downstream diagnostic and analytical applications.

In continued reference to FIG. 1, in an embodiment, workflow management as described herein may be consistent with one or more aspects of workflow management as described in U.S. patent application Ser. No. 19/050,842, filed on Feb. 2, 2025, entitled "APPARATUS AND METHOD FOR RESCAN WORKFLOW MANAGEMENT IN AUTOMATED SCANNING SYSTEMS," which is incorporated by reference herein in its entirety.

Figure 2:
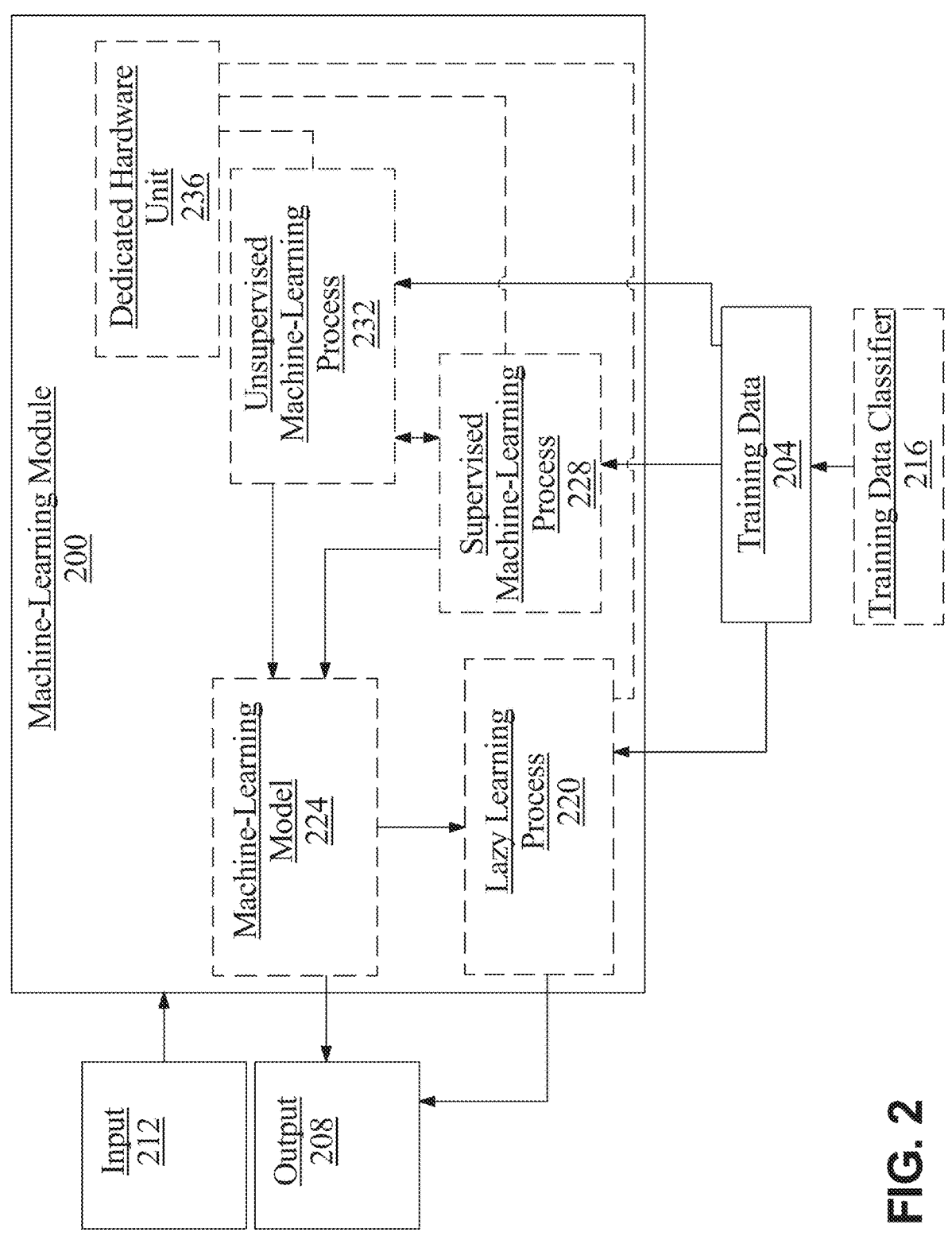
FIG. 2 is a block diagram of an exemplary embodiment of a machine learning model.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example inputs may include imaging data, whereas outputs may include a target profile 144.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to cohorts associated with target types and associated imaging parameters.

Still referring to FIG. 2, a computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)$ $P(A)=P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. A computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, a computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 2, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. A computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 2, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 2, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 2, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max} : X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between $X$ and $X_{mean}$ is divided by a standard deviation $\sigma$ of a set or subset of values:

$$X_{new} = \frac{X - X_{mean}}{\sigma}.$$

Scaling may be performed using a median value of a set or subset $X_{median}$ and/or interquartile range (IQR), which represents the difference between the 25th percentile value and the 50th percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 2, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228.

At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described above as inputs, outputs described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3:
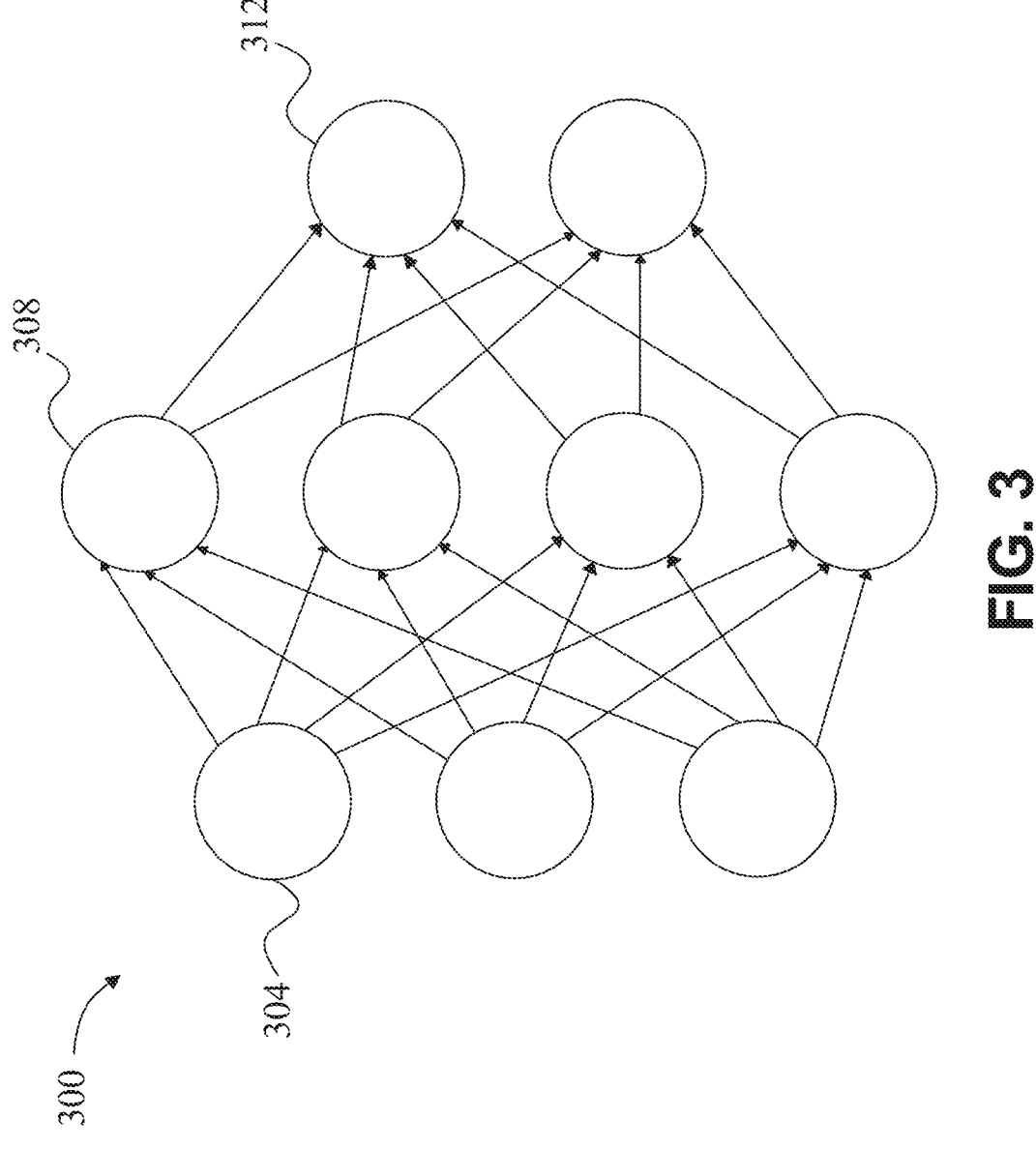
FIG. 3 is a schematic diagram of an exemplary embodiment of a neural network.

Referring now to FIG. 3, an exemplary embodiment of neural network 300 is illustrated. A neural network 300 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 4:
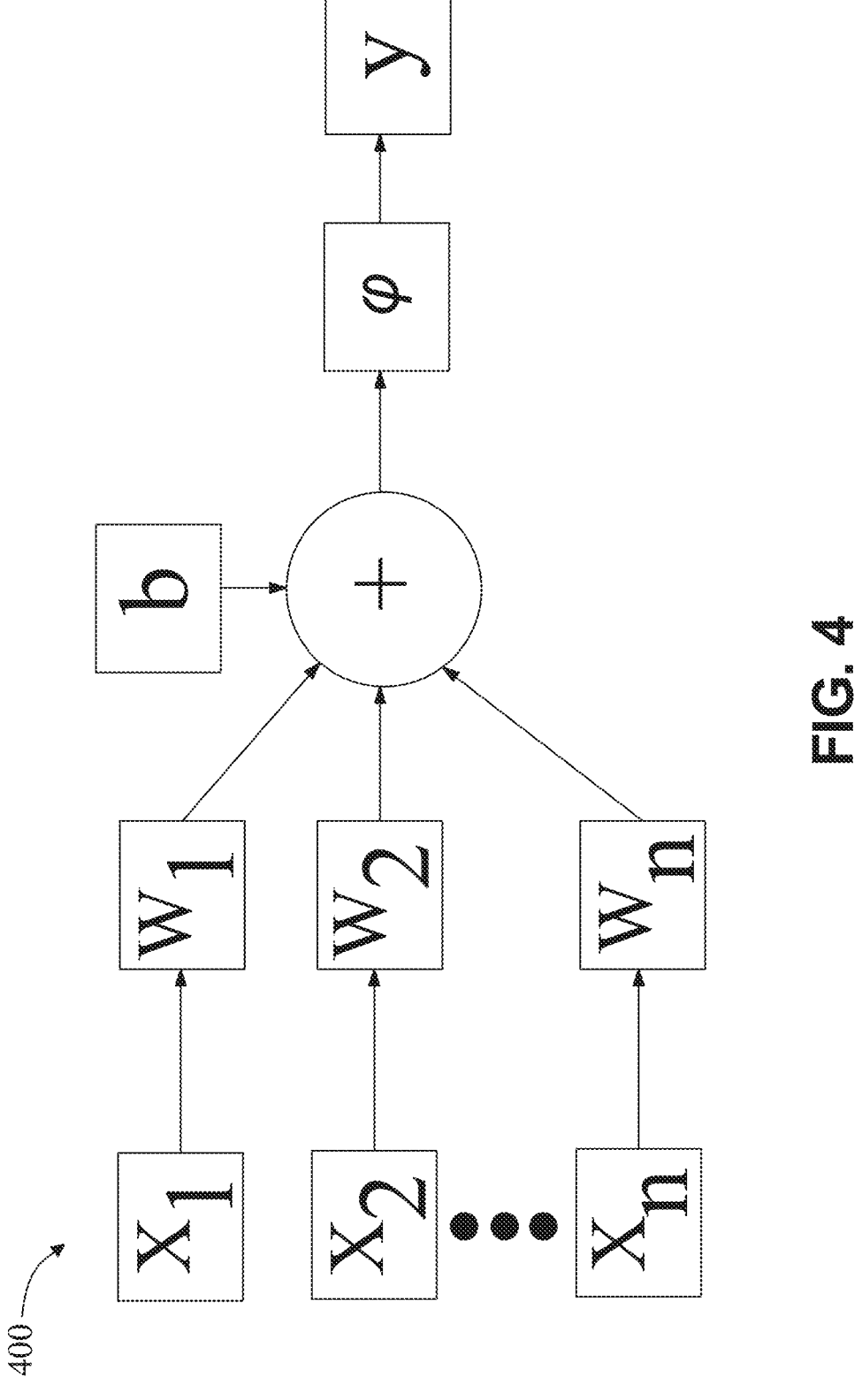
FIG. 4 is a schematic diagram of an exemplary embodiment of a neural network node.

Referring now to FIG. 4, an exemplary embodiment of a node 400 of a neural network is illustrated. A node may include, without limitation a plurality of inputs xi that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of $\alpha$ (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $d(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs x; that may be used as activation functions. As a non-limiting and illustrative example, node may perform a weighted sum of inputs using weights $w_i$ that are multiplied by respective inputs $x_i$. Additionally, or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Referring now to FIG. 5A-C, a slide progressing through various steps described herein is illustrated. A slide 504 may contain annotations 508A-B, debris 512A-B, and sample 516A-B. Steps described herein may address a challenge of choosing a correct focus for a region where a sample is present despite the presence of debris and annotations. Segmenting slide 504 into separate regions of interest 520A-F enables scanning each segment with a different focus optimal to that region. This makes the focus determination independent of the spatial distribution of the sample, debris, and annotations. In some embodiments, image classification for detecting debris and annotations to avoid scanning may be best done downstream as opposed to during scanning. In some embodiments, this may resolve the challenge of running sophisticated models on a scanning device live during a scan, and the risk of false positives when classifying a region as debris or annotation and skipping a scan of a relevant region. Also, annotations may be useful for downstream tasks may need to be scanned for use in multimodal learning downstream. In some embodiments, segmentation followed by best focus determination may be a beneficial approach for detecting all regions of interest at the optimal focus obtained by best row estimation.

Referring now to FIG. 6, an exemplary method 600 for automated profile identification is illustrated. Method 600 may include a step 605 of controlling at least an imaging device to pre-scan a target. In an embodiment, at least an imaging device may include a plurality of imaging devices configured to simultaneously capture imaging data of a plurality of targets. This may be implemented, without limitation, as referenced in FIGS. 1-5.

With further reference to FIG. 6, method 600 may include a step 610 of receiving, from at least an imaging device by at least a processor, pre-scan imaging data. In an embodiment, receiving from at least an imaging device, the pre-scan imaging data may include segmenting the pre-scan imaging data using a segmentation algorithm. This may be implemented, without limitation, as referenced in FIGS. 1-5.

In continued reference to FIG. 6, method 600 may include a step 615 of detecting a position of a fiducial marker within the pre-scan imaging data. This may be implemented, without limitation, as referenced in FIGS. 1-5.

With continued reference to FIG. 6, method 600 may include a step 620 of inputting the pre-scan imaging data into a feature-learning neural network. This may be implemented, without limitation, as referenced in FIGS. 1-5.

In further reference to FIG. 6, method 600 may include a step 625 of outputting at least an image feature from the feature-learning neural network as a function of the pre-scan imaging data, wherein the at least a feature represents at least a specimen type. This may be implemented, without limitation, as referenced in FIGS. 1-5.

With further reference to FIG. 6, method 600 may include a step 630 of selecting a target profile including one or more imaging parameters as a function of the specimen type and the fiducial marker, wherein the target profile includes one or more imaging parameters. In an embodiment, the target profile may include an imaging mode including one or more imaging parameters selected from a group of resolution, exposure time, illumination intensity, and scanning speed, and the imaging mode is selected as a function of the specimen type to optimize image acquisition of the target. In an embodiment, the target profile may further include a focus strategy, wherein the focus strategy includes determining an optimal focal place as a function of the target, and adjusting focus parameters as a function of the optimal focal plane. In an embodiment, step 625 may be accomplished using a classification model configured to classify the at least a feature into a target. In an embodiment, the classification model may be trained on a dataset including images of various target types, wherein target types include blood smears, cytology samples, and biopsy samples. In an embodiment, the classification model may be trained on a dataset including images of various target types, wherein target types may include one or more of microbiology samples, hematology samples, cytology samples, and histopathology samples. This may be implemented, without limitation, as referenced in FIGS. 1-5.

In continued reference to FIG. 6, method 600 may include a step 635 of adjusting, using the target profile, an imaging device configuration as a function of the one or more imaging parameters. This may be implemented, without limitation, as referenced in FIGS. 1-5.

With further reference to FIG. 6, method 600 may further include receiving high magnification imaging feedback from the at least an imaging device and verify and correct a predicted target profile as a function of the high magnification imaging feedback. In an embodiment, correcting a predicted target profile as a function of the high magnification imaging feedback may include generating refined profile classification data using the high magnification imaging feedback and a classification model, comparing the refined profile and corresponding one or more imaging parameters as a function of comparing the refined profile classification data and the predicted target profile. This may be implemented, without limitation, as referenced in FIGS. 1-5.

Still referring to FIG. 6, method 600 may further include performing inline validation, wherein performing inline validation includes periodically capturing images of reference targets and comparing the images of reference targets against pre-defined imaging standards to verify and maintain imaging accuracy. This may be implemented, without limitation, as referenced in FIGS. 1-5.

In further reference to FIG. 6, method 600 may further include extracting data from the target using optical character recognition, wherein the target comprises a slide label and the extracted data is used to select the target profile. This may be implemented, without limitation, as referenced in FIGS. 1-5.

With continued reference to FIG. 6, method 600 may further include a step of capturing imaging data, using at least an imaging device, as a function of one or more imaging parameters determined from pre-scan imaging data. In an embodiment, this may include receiving high magnification imaging feedback from at least an imaging device and verifying and correcting a predicted target profile as a function of high magnification imaging feedback. In an embodiment, verifying and correcting a predicted target profile as a function of high magnification imaging feedback may include generating refined profile classification data using high magnification imaging feedback and classification model. In an embodiment, verifying and correcting a predicted target profile as a function of high magnification imaging feedback may include comparing refined profile classification data and predicted target profile. In an embodiment, verifying and correcting a predicted target profile as a function of high magnification imaging feedback may include updating predicted target profile and corresponding one or more imaging parameters as a function of comparing refined profile classification data and predicted target profile. This may be implemented, without limitation, as referenced in FIGS. 1-5.

In further reference to FIG. 6, method 600 may further include a step of performing inline validation. Wherein, inline validation includes periodically capturing images of reference targets and comparing the images of reference targets against pre-defined imaging standards to verify and maintain accuracy. This may be implemented, without limitation, as referenced in FIGS. 1-5.

With continued reference to FIG. 6, method 600 may further include a step of scheduling, monitoring, and logging scanning operations using a workflow management module and providing automated notifications as a function of an imaging process. This may be implemented, without limitation, as referenced in FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
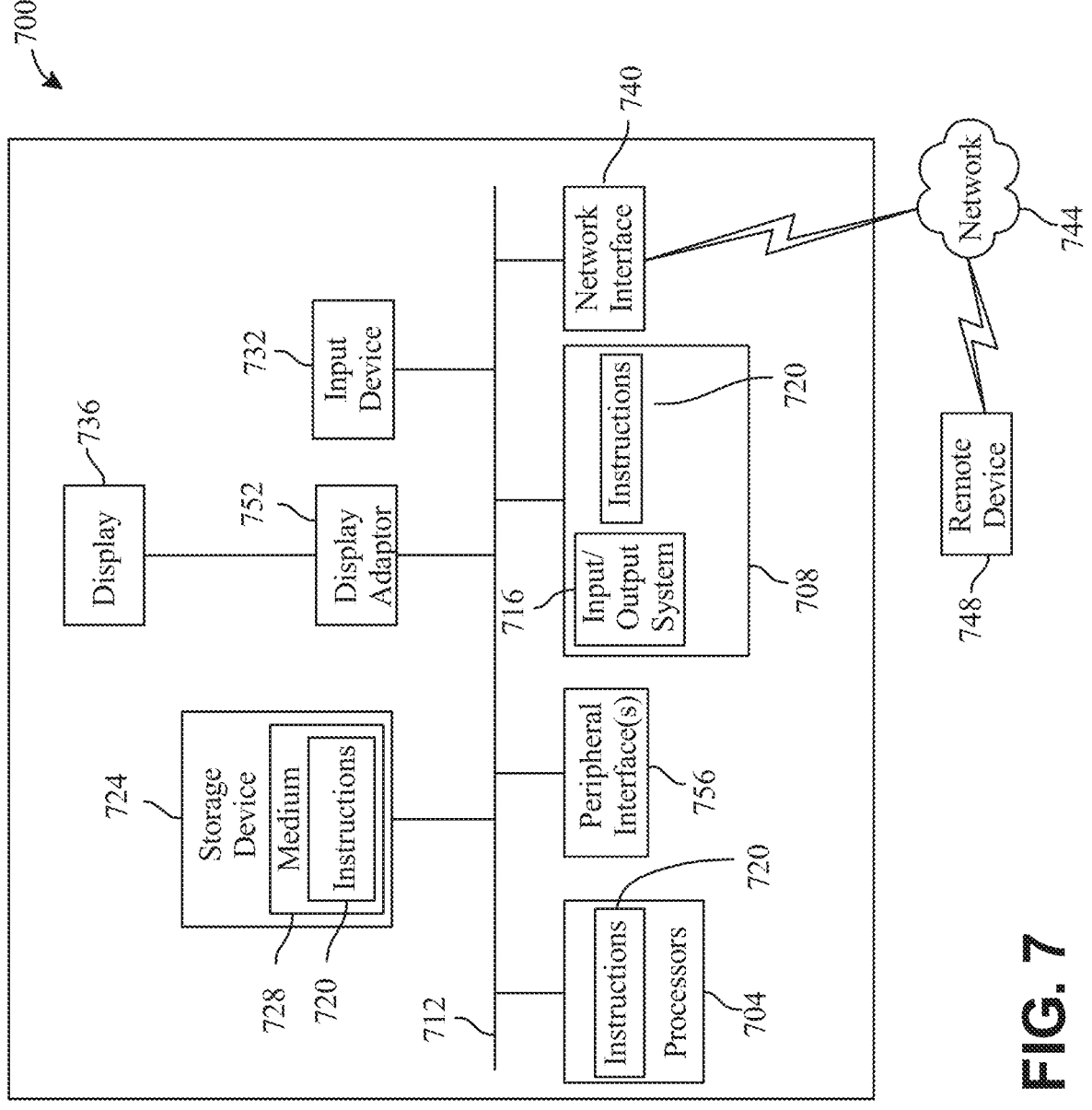
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIRE-WIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for automated target profile identification, wherein the system comprises:
at least an imaging device configured to pre-scan a target to generate pre-scan imaging data, wherein the target comprises a fiducial marker; and
a computing device communicatively connected to the at least an imaging device,
wherein the computing device comprises:
at least a processor; and
a memory communicatively connected to the at least a processor, wherein the memory contains instructions configuring the at least a processor to:
control the at least an imaging device while pre-scanning the target;
receive, from the at least an imaging device, the pre-scan imaging data;
detect a position of the fiducial marker within the pre-scan imaging data;
input the pre-scan imaging data into a feature-learning neural network;
output at least an image feature from the feature-learning neural network, as a function of the pre-scan imaging data, wherein the at least a feature represents at least a specimen type;
select a target profile as a function of the specimen type and the fiducial marker, wherein the target profile comprises one or more imaging parameters; and
adjust, using the target profile, an imaging device configuration as a function of the one or more imaging parameters;
capture, using the at least an imaging device, imaging data as a function of the one or more imaging parameters determined from the pre-scan imaging data;
receive, using the at least a processor, high magnification imaging feedback from the at least an imaging device; and
verify and correct, using the at least a processor, a predicted target profile as a function of the high magnification imaging feedback.

2. The system of claim 1, wherein receiving, from the at least an imaging device, the pre-scan imaging data comprises segmenting the pre-scan imaging data using a segmentation algorithm.

3. The system of claim 1, wherein the at least an imaging device comprises a plurality of imaging devices configured to simultaneously capture imaging data of a plurality of targets.

4. The system of claim 1, wherein:
the target profile comprises an imaging mode comprising one or more imaging parameters selected from a group of resolution, exposure time, illumination intensity, and scanning speed; and
the imaging mode is selected as a function of the specimen type to optimize image acquisition of the target.

5. The system of claim 1, wherein the target profile comprises a focus strategy, wherein the focus strategy comprises:
determining an optimal focal plane as a function of the target; and
adjusting focus parameters as a function of the optimal focal plane.

6. The system of claim 1, wherein verifying and correcting a predicted target profile as a function of the high magnification imaging feedback comprises:
generating refined profile classification data using the high magnification imaging feedback and a classification model;
comparing the refined profile classification data and the predicted target profile; and
updating the predicted target profile and corresponding one or more imaging parameters as a function of comparing the refined profile classification data and the predicted target profile.

7. The system of claim 1,
wherein the at least a processor is further configured to classify, using a classification model, the at least a feature into a target type; and
wherein, the classification model is trained on a dataset comprised of images of target types, wherein the target types comprise one or more of microbiology samples, hematology samples, cytology samples, and histopathology samples.

8. The system of claim 1, wherein the at least a processor is further configured to extract data from the target using optical character recognition, wherein:
the target comprises a slide label; and
the extracted data is used to select the target profile.

9. A method for automated target profile identification, wherein the method comprises:
controlling the at least an imaging device while pre-scanning a target;
receiving, from the at least an imaging device, pre-scan imaging data comprising a fiducial marker;
detecting a position of the fiducial marker within the pre-scan imaging data;
inputting the pre-scan imaging data into a feature-learning neural network;
outputting at least an image feature from the feature-learning neural network, as a function of the pre-scan imaging data, wherein the at least a feature represents at least a specimen type;
selecting a target profile as a function of the specimen type and the fiducial marker, wherein the target profile comprises one or more imaging parameters; and adjusting, using the target profile, an imaging device configuration as a function of the one or more imaging parameters; and capturing, using the at least an imaging device, imaging data, as a function of the one or more imaging parameters determined from the pre-scan imaging data;

receiving, by the at least a processor, high magnification imaging feedback from the at least an imaging device; and verifying and correcting a predicted target profile as a function of the high magnification imaging feedback.

10. The method of claim 9, wherein receiving, from the at least an imaging device, the pre-scan imaging data comprises segmenting the pre-scan imaging data using a segmentation algorithm.

11. The method of claim 9, wherein the at least an imaging device comprises a plurality of imaging devices configured to simultaneously capture imaging data of a plurality of targets.

12. The method of claim 9, wherein:

the target profile comprises an imaging mode comprising one or more imaging parameters selected from a group of resolution, exposure time, illumination intensity, and scanning speed; and the imaging mode is selected as a function of the specimen type to optimize image acquisition of the target.

13. The method of claim 9, wherein the target profile comprises a focus strategy, wherein the focus strategy comprises:

determining an optimal focal plane as a function of the target; and adjusting focus parameters as a function of the optimal focal plane.

14. The method of claim 9, wherein verifying and correcting a predicted target profile as a function of the high magnification imaging feedback comprises:

generating refined profile classification data using the high magnification imaging feedback and a classification model;

comparing the refined profile classification data and the predicted target profile; and updating the predicted target profile and corresponding one or more imaging parameters as a function of comparing the refined profile classification data and the predicted target profile.

15. The method of claim 9, further comprising classifying the at least a feature into a target type using a classification model, wherein the classification model is trained on a dataset comprised of images of target types, wherein the target types comprise one or more of microbiology samples, hematology samples, cytology samples, and histopathology samples.

16. The method of claim 9, further comprising extracting data from the target using optical character recognition, wherein:

the target comprises a slide label; and the extracted data is used to select the target profile.

17. A system for automated target profile identification, wherein the system comprises:

at least an imaging device configured to pre-scan a target to generate pre-scan imaging data, wherein the target comprises a fiducial marker; and a computing device communicatively connected to the at least an imaging device, wherein the computing device comprises:

at least a processor; and a memory communicatively connected to the at least a processor, wherein the memory contains instructions configuring the at least a processor to:

control the at least an imaging device while pre-scanning the target;

receive, from the at least an imaging device, the pre-scan imaging data;

detect a position of the fiducial marker within the pre-scan imaging data;

input the pre-scan imaging data into a feature-learning neural network;

output at least an image feature from the feature-learning neural network, as a function of the pre-scan imaging data, wherein the at least a feature represents at least a specimen type;

select a target profile as a function of the specimen type and the fiducial marker, wherein the target profile comprises one or more imaging parameters; and adjust, using the target profile, an imaging device configuration as a function of the one or more imaging parameters;

perform inline validation, wherein performing inline validation comprises:

periodically capturing images of reference targets; and comparing the images of reference targets against pre-defined imaging standards to verify and maintain imaging accuracy.

18. A method for automated target profile identification, wherein the method comprises:

controlling the at least an imaging device while pre-scanning a target;

receiving, from the at least an imaging device, pre-scan imaging data comprising a fiducial marker;

detecting a position of the fiducial marker within the pre-scan imaging data;

inputting the pre-scan imaging data into a feature-learning neural network;

outputting at least an image feature from the feature-learning neural network, as a function of the pre-scan imaging data, wherein the at least a feature represents at least a specimen type;

selecting a target profile as a function of the specimen type and the fiducial marker, wherein the target profile comprises one or more imaging parameters; and adjusting, using the target profile, an imaging device configuration as a function of the one or more imaging parameters; and performing inline validation, wherein performing inline validation comprises:

periodically capturing images of reference targets; and comparing the images of reference targets against pre-defined imaging standards to verify and maintain imaging accuracy.

* * * * *